US006183738B1

(12) United States Patent
Clark

(10) Patent No.: US 6,183,738 B1
(45) Date of Patent: Feb. 6, 2001

(54) MODIFIED ARGININE DEIMINASE

(75) Inventor: Mike A. Clark, Big Pine, FL (US)

(73) Assignee: Phoenix Pharamacologics, Inc., Exton, PA (US)

( * ) Notice: Under 35 U.S.C. 154(b), the term of this patent shall be extended for 0 days.

(21) Appl. No.: 09/023,809

(22) Filed: Feb. 13, 1998

Related U.S. Application Data
(60) Provisional application No. 60/046,200, filed on May 12, 1997.

(51) Int. Cl.[7] .............................. A61K 38/44; C12N 9/06; C12N 9/96; C12N 11/06; C12N 11/08

(52) U.S. Cl. ........................ 424/94.4; 435/180; 435/188; 435/191; 435/181

(58) Field of Search ................................... 435/180, 181, 435/188, 191; 424/94.4

(56) References Cited

U.S. PATENT DOCUMENTS

| | | | |
|---|---|---|---|
| 4,179,337 | 12/1979 | Davis et al. | 435/181 |
| 4,609,546 | 9/1986 | Hiratani | 424/83 |
| 5,372,942 | * 12/1994 | McGarrity et al. | 435/227 |
| 5,447,722 | 9/1995 | Lang et al. | 424/280.1 |
| 5,468,478 | 11/1995 | Saifer et al. | 424/78.27 |
| 5,474,928 | 12/1995 | Takaku et al. | 435/228 |
| 5,804,183 | * 8/1998 | Filpula et al. | 424/94.6 |

FOREIGN PATENT DOCUMENTS

| | | |
|---|---|---|
| 0 372 752 A2 | 6/1990 | (EP) . |
| 53490 | 2/1990 | (JP) . |
| 4-121187 | 4/1992 | (JP) . |
| 94/05332 | 3/1994 | (WO) . |
| 96/34015 | 10/1996 | (WO) . |

OTHER PUBLICATIONS

Pierce, "Handbook & General Catalog", pp. 283–311, 1989.*

Abuchowski, A. et al., "Effect of Covalent Attachment of Polyethylene Glycol on Immunogenicity and Circulating Life of Bovine Liver Catalase", *J. Biol. Chem.*, 1977, 252(11),3582–3586.

Abuchowski, A. et al., "Treatment of L5178Y Tumor–Bearing BDF Mice with a Nonimmunogneic L–Glutaminase–L–Asparaginase", *Cancer Treat. Rep.*, 1979, 63(6), 1127–1132.

Gill, P. et al., "Inhibition of cell division in L5178Y cells by arginine–degrading mycoplasmas: the role of arginine deiminase", *Can J. Microbiol.*, 1970, 16, 415–419.

Habeeb, A.F.S.A, "Determination of Free Amino Groups in Proteins by Trinitrobenzenesulfonic Acid ", *Analyt. Biochem.*, 1996, 14, 328–336.

Hershfield, M.S. et al., "Treatment of Adenosine Deaminase Deficiency with Polyethylene Glycol–Modified Adenosine Deaminase", *New Engl. J. Medicine*, 1987, 316(10), 589–596.

Jaffe, N. et al., "Favorable Remission Induction Rate with Twice Weekly Doses of L–Asparaginase", *Cancer Res.*, 1973, 33(1), 1–4.

Jones, J.B., "The Effect of Arginine Deiminase on Murine Leukemic Lymphoblasts", Ph.D Dissertation, The University of Oklahoma, 1981, 1–165.

Kamisaki et al., "Increased Antitumor Activity of *Escherichia Coli* L–Asparaginase By Modification with Monomethoxypolyethylene Glycol", *Gann.*, 1982, 73, 470–474.

Kamisaki et al., "Reduction in Immunogenicity and Clearance Rate of *Escherichia coli* L–Asparaginase by Modification with Monomethoxypolyethylene Glycol", *J. Pharmacol. Exp. Ther.*, 1981, 216(2), 410–414.

Kidd, J.G., "Asparaginase and Cancer—Yesterday and Today", *Cancer Res.*, 1970, 33, 1–14.

Kondo, K. et al., "Cloning and sequence analysis of the arginine deiminase gene from *Mycoplasma arginini*", *Mol. Gen. Genet.*, 1990, 221, 81–86.

Misawa, S. et al., "High–level expression of Mycoplasma arginine deiminase in *Escherichia coli* and its efficient renaturation as an anti–tumor enzyme", *J. Biotechnology*, 1994, 36, 145–155.

Miyasaki, K. et al., "Potent Growth Inhibition of Human Tumor Cells in Culture by Arginine Deiminase Purified from a Culture of a Mycoplasma–infected Cell Line", *Cancer Res.*, 50, 4522–4527.

Monfardini, C. et al., "A Branched Monomethoxypoly(ethylene glycol) for Protein Modification", *Bioconj. Chem.*, 1995, 6, 62–69.

Naoi, M. et al., "Alteration of the Substrate Specificity of *Aspergillus oryzae* β–Galactsidase by Modification with Polyethylene Gycol", *J. Appl. Biochem.*, 1984, 6, 91–102.

Oginsky, "[92] Isolation and Determination of Arginine and Citrulline", *Meth. Enzymol.* , 1957, 3, 639–642.

Ohno, T. et al., "Cloning and Nucleotide Sequence of the Gene Encoding Arginine Deiminase of *Mycoplasma arginini*", *Infect. Immun.*, 1990, 58, 3788–3795.

Park, Y.K. et al., "Pharmacology of *Escherichia Coli–L–Asparaginase* Polyethylene Gycol Adduct", *Anticancer Res.*, 1981, 1, 373–376.

Pyatak, P.S. et al., "Preparation of a Polyethylene Gycol: Superoxide Dismutase Adduct, and an Examination of its Blood Circulating Life and Anti–Inflammatory Activity", *Res. Commun. Chem. Path. Pharmacol.*, 1980, 29(1), 113–127.

Sayers, J.R. et al., "Rapid High–Efficiency Site–Directed Mutagenesis by the Phosphorothioate Approach", *Biotechniques*, 1992, 13(4), 592–596.

(List continued on next page.)

Primary Examiner—Jon P. Weber
(74) Attorney, Agent, or Firm—Woodcock Washburn Kurtz Mackiewicz & Norris LLP

(57) ABSTRACT

The present invention is directed to arginine deiminase modified with polyethylene glycol, to methods of treating cancer, and to methods of treating and/or inhibiting metastasis.

22 Claims, 6 Drawing Sheets

OTHER PUBLICATIONS

Stocks, S.J. et al., "A Fluorometric Assay of the Degree of Modification of Protein Primary Amines with Polyethylene Gycol", *Analyt. Biochem.*, 1986, 154, 232–234.

Su, T. et al., "Cloning of cDNA for Argininosuccinate Synthetase mRNA and Study of Enzyme Overproduction in a Human Cell Line", *J. Biol. Chem.*, 1981, 256(22), 11826–11831.

Sugimura, K. et al., "High sensitivity of human melanoma cell lines of growth inhibitory activity of mycoplasmal arginine deiminase in vitro", *Melanoma Res.*, 1992, 2, 191–196.

Sugimura, K. et al., "Identification and Purification of Arginine Deiminase That Orginated from *Mycoplasma arginini*", *Infect. Immun.*, 1990, 58(8), 2510–2515.

Takaku, H. et al., "Anti–Tumor Activity of Arginine Deiminase From *Mycoplasma Arginini* and Its Growth–inhibitory Mechanism", *Int. J. Cancer*, 1995, 86, 840–846.

Takaku, H. et al., "In Vivo Anti–Tumor Activity of Arginine Deiminase Purified From *Mycoplasma Arginini*", *Int. J. Cancer*, 1992, 51, 244–249.

Takaku, H. et al., "Chemical Modification by Polyethylene Gycol of the Anti–tumor Enzyme Arginine Deiminase from *Mycoplasma arginini*", *Jpn. J. Cancer Res.*, 1993, 84, 1195–1200.

Teske, E. et al., "Polyethylene Gycol–L–asparaginase versus Native L–asparaginase in Canine Non–Hodgkin's Lymphoma", *Eur. J. Cancer*, 1990, 26(8), 891–895.

Zaplipksy et al., "Use of Functionalized Poly(Ethylene Gycol)s for Modification of Polypeptides", *Polyethylene Gycol Chemistry: Biotechnical and Biomedical Applications*, J.M. Harris (ed.), Plenum Press, NY, 1992, Chapter 21, 347–370.

\* cited by examiner

The alignment was done on 3 Protein sequences.
Character to show that a position in the alignment is perfectly conserved: '*'
Character to show that a position is well conserved: '.'

Alignment

```
ADIPROT    MSVFDSKFKGIHVYSEIGELESVLVHEPGREIDYITPARLDELLFSAILE    50
ARTADIPRO  MSVFDSKFKGIHVYSEIGELESVLVHEPGREIDYITPARLDELLFSAILE    50
HOMADIPRO  MSVFDSKFNGIHVYSEIGELETVLVHEPGREIDYITPARLDELLFSAILE    50
           *******.**********.*******************************

ADIPROT    SHDARKEHKQFVAELKANDINVVELIDLVAETYDLASQEAKDKLIEEFLE    100
ARTADIPRO  SHDARKEQSQFVAILKANDINVVETIDLVAETYDLASQEAKDRLIEEFLE    100
HOMADIPRO  SHDARKEHQSFVKIMKDRGINVVELTDLVAETYDLASKAAKEEFIETFLE    100
           *******. **  .*...***** .***********..**.**.***

ADIPROT    DSEPVLSEEHKVVVRNFLKAKKTSRKLVEIMMAGITKYDLGIEADHELIV    150
ARTADIPRO  DSEPVLSEAHKKVVRNFLKAKKTSRKLVELMMAGITKYDLGVEADHELIV    150
HOMADIPRO  ETVPVLTEANKKAVRAFLLSKPT-HEMVEFMMSGITKYELGVESENELIV    149
           .. ***.*..* .**.**  . *   ...**.**.*****.**.*...****

ADIPROT    DPMPNLYFTRDPFASVGNGVTIHYMRYKVRQRETLFSRFVFSNHPKLINT    200
ARTADIPRO  DPMPNLYFTRDPFASVGNGVTIHFMRYKVRRRETLFSRFVFRNHPKLVNT    200
HOMADIPRO  DPMPNLYFTRDPFASVGNGVTIHFMRYIVRRRETLFARFVFRNHPKLVKT    199
           ***********************.***.**.*****.****.*****..*

ADIPROT    PWYYDPSLKLSIEGGDVFIYNNDTLVVGVSERTDLQTVTLLAKNIVANKE    250
ARTADIPRO  PWYYDPAMKLSIEGGDVFIYNNDTLVVGVSERTDLDTVTLLAKNLVANKE    250
HOMADIPRO  PWYYDPAMKMPIEGGDVFIYNNETLVVGVSERTDLDTITLLAKNIKANKE    249
           ******..*..***********.***********.*.******. ****

ADIPROT    CEFKRIVAINVPKWTNLMHLDTWLTMLDKDKFLYSPIANDVFKFWDYDLV    300
ARTADIPRO  CEFKRIVAINVPKWTNLMHLDTWLTMLDKNKFLYSPIANDVFKFWDYDLV    300
HOMADIPRO  VEFKRIVAINVPKWTNLMHLDTWLTMLDKNKFLYSPIANDVFKFWDYDLV    299
            ***************************.*********************

ADIPROT    NGGAEPQPVENGLPLEGLLQSIINKKPVLIPIAGEGASQMEIERETHFDG    350
ARTADIPRO  NGGAEPQPVENGLPLEKLLQSIINKKPVLIPIAGEGASQMEIERETHFDG    350
HOMADIPRO  NGGAEPQPQLNGLPLDKLLASIINKEPVLIPIGGAGATEMEIARETNFDG    349
           ********  ****. ** *****.*******.*.**.****.***.***

ADIPROT    TNYLAIRPGVVIGYSRNEKTNAALEAAGIKVLPFHGNQLSLGMGNARCMS    400
ARTADIPRO  TNYIAIRPGVVIGYSRNEKTNAALKAAGIKVLPFHGNQLSLGMGNARCMS    400
HOMADIPRO  TNYLAIKPGLVIGYDRNEKTNAALKAAGITVLPFHGNQLSLGMGNARCMS    399
           ***.**.**.****.********.****.*********************

ADIPROT    MPLSRKDVK    409
ARTADIPRO  MPLSRKDVK    409
HOMADIPRO  MPLSRKDVK    408
           *********
```

FIG. 1

| ADIPROT | = Mycoplasma arginini |
| ARTADIPRO | = Mycoplasma arthritides |
| HOMADIPRO | = Mycoplasma hominus |

SEQUENCE LISTING

<160> NUMBER OF SEQ ID NOS: 5

<210> SEQ ID NO 1
<211> LENGTH: 409
<212> TYPE: PRT
<213> ORGANISM: Mycoplasma arginini

<400> SEQUENCE: 1

```
Met Ser Val Phe Asp Ser Lys Phe Lys Gly Ile His Val Tyr Ser Glu
  1               5                  10                  15

Ile Gly Glu Leu Glu Ser Val Leu Val His Glu Pro Gly Arg Glu Ile
             20                  25                  30

Asp Tyr Ile Thr Pro Ala Arg Leu Asp Glu Leu Leu Phe Ser Ala Ile
         35                  40                  45

Leu Glu Ser His Asp Ala Arg Lys Glu His Lys Gln Phe Val Ala Glu
     50                  55                  60

Leu Lys Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Lys Leu Ile Glu
                 85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Lys Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220
```

-continued

```
Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 2
<211> LENGTH: 409
<212> TYPE: PRT
<213> ORGANISM: Mycoplasma arthritidis

<400> SEQUENCE: 2

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu Gln Ser Gln Phe Val Ala Ile
    50                  55                  60

Leu Lys Ala Asn Asp Ile Asn Val Val Glu Thr Ile Asp Leu Val Ala
65                  70                  75                  80

Glu Thr Tyr Asp Leu Ala Ser Gln Glu Ala Lys Asp Arg Leu Ile Glu
                85                  90                  95

Glu Phe Leu Glu Asp Ser Glu Pro Val Leu Ser Glu Ala His Lys Lys
            100                 105                 110

Val Val Arg Asn Phe Leu Lys Ala Lys Lys Thr Ser Arg Lys Leu Val
        115                 120                 125

Glu Leu Met Met Ala Gly Ile Thr Lys Tyr Asp Leu Gly Val Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Lys Val Arg Arg Arg Glu Thr Leu Phe Ser Arg Phe Val Phe Arg
```

```
                180             185             190
Asn His Pro Lys Leu Val Asn Thr Pro Trp Tyr Tyr Asp Pro Ala Met
        195                 200                 205
Lys Leu Ser Ile Glu Gly Gly Asp Val Phe Ile Tyr Asn Asn Asp Thr
    210                 215                 220
Leu Val Val Gly Val Ser Glu Arg Thr Asp Leu Asp Thr Val Thr Leu
225                 230                 235                 240
Leu Ala Lys Asn Leu Val Ala Asn Lys Glu Cys Glu Phe Lys Arg Ile
            245                 250                 255
Val Ala Ile Asn Val Pro Lys Trp Thr Asn Leu Met His Leu Asp Thr
                260                 265                 270
Trp Leu Thr Met Leu Asp Lys Asn Lys Phe Leu Tyr Ser Pro Ile Ala
        275                 280                 285
Asn Asp Val Phe Lys Phe Trp Asp Tyr Asp Leu Val Asn Gly Gly Ala
    290                 295                 300
Glu Pro Gln Pro Val Glu Asn Gly Leu Pro Leu Glu Lys Leu Leu Gln
305                 310                 315                 320
Ser Ile Ile Asn Lys Lys Pro Val Leu Ile Pro Ile Ala Gly Glu Gly
            325                 330                 335
Ala Ser Gln Met Glu Ile Glu Arg Glu Thr His Phe Asp Gly Thr Asn
                340                 345                 350
Tyr Ile Ala Ile Arg Pro Gly Val Val Ile Gly Tyr Ser Arg Asn Glu
        355                 360                 365
Lys Thr Asn Ala Ala Leu Lys Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys
                405

<210> SEQ ID NO 3
<211> LENGTH: 408
<212> TYPE: PRT
<213> ORGANISM: Mycoplasma hominis

<400> SEQUENCE: 3

Met Ser Val Phe Asp Ser Lys Phe Asn Gly Ile His Val Tyr Ser Glu
1               5                   10                  15
Ile Gly Glu Leu Glu Thr Val Leu Val His Glu Pro Gly Arg Glu Ile
            20                  25                  30
Asp Tyr Ile Thr Pro Ala Arg Leu Asp Glu Leu Leu Phe Ser Ala Ile
        35                  40                  45
Leu Glu Ser His Asp Ala Arg Lys Glu His Gln Ser Phe Val Lys Ile
    50                  55                  60
Met Lys Asp Arg Gly Ile Asn Val Val Glu Leu Thr Asp Leu Val Ala
65                  70                  75                  80
Glu Thr Tyr Asp Leu Ala Ser Lys Ala Ala Lys Glu Glu Phe Ile Glu
            85                  90                  95
Thr Phe Leu Glu Glu Thr Val Pro Val Leu Thr Glu Ala Asn Lys Lys
            100                 105                 110
Ala Val Arg Ala Phe Leu Leu Ser Lys Pro Thr His Glu Met Val Glu
        115                 120                 125
Phe Met Met Ser Gly Ile Thr Lys Tyr Glu Leu Gly Val Glu Ser Glu
    130                 135                 140
```

```
-continued

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
            165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
            195                 200                 205

Met Pro Ile Glu Gly Gly Asp Val Phe Ile Tyr Asn Asn Glu Thr Leu
            210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
            245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
            275                 280                 285

Asp Val Phe Lys Phe Trp Asp Tyr Asp Leu Val Asn Gly Gly Ala Glu
290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
            325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
            370                 375                 380

Gly Asn Gln Leu Ser Leu Gly Met Gly Asn Ala Arg Cys Met Ser Met
385                 390                 395                 400

Pro Leu Ser Arg Lys Asp Val Lys
                405

<210> SEQ ID NO 4
<211> LENGTH: 23
<212> TYPE: DNA
<213> ORGANISM: Mycoplasma arginini

<400> SEQUENCE: 4
gcaatcgatg tgtatttgac agt                                              23

<210> SEQ ID NO 5
<211> LENGTH: 33
<212> TYPE: DNA
<213> ORGANISM: Mycoplasma arginini

<400> SEQUENCE: 5
tgaggatcct tactaccact taacatcttt acg                                   33
```

MODIFIED ARGININE DEIMINASE

RELATED APPLICATIONS

This application claims priority benefit to U.S. Provisional Patent Application Ser. No. 60/046,200, filed on May 12, 1997.

FIELD OF THE INVENTION

The present invention is directed to arginine deiminase modified with polyethylene glycol, to methods for treating cancer, and to methods for treating and/or inhibiting metastasis.

BACKGROUND OF THE INVENTION

Malignant melanoma (stage 3) and hepatoma are fatal diseases which kill most patients within one year of diagnosis. In the United States, approximately 16,000 people die from these diseases annually. The incidence of melanoma is rapidly increasing in the United States and is even higher in other countries, such as Australia. The incidence of hepatoma, in parts of the world where hepatitis is endemic, is even greater. For example, hepatoma is one of the leading forms of cancer in Japan and Taiwan. Effective treatments for these diseases are urgently needed.

Selective deprivation of essential amino acids has been used to treat some forms of cancer. The best known example is the use of L-asparaginase to lower levels of asparagine as a treatment for acute lymphoblastic leukemia. The L-asparaginase most frequently used is isolated from *E. coli*. However, clinical use of this enzyme is compromised by its inherent antigenicity and short circulating half-life, as described by Y. K. Park, et al, *Anticancer Res.*, 1:373–376 (1981). Covalent modification of *E. coli* L-asparaginase with polyethylene glycol reduces its antigenicity and prolongs its circulating half-life, as described, for example, by Park, *Anticancer Res.*, supra; Y. Kamisaki et al, *J. Pharmacol. Exp. Ther.*, 216:410–414 (1981); and Y. Kamisaki et al, *Gann.*, 73:47–474 (1982). Although there has been a great deal of effort to identify other essential amino acid degrading enzymes for the treatment of cancer, none have been approved, primarily because deprivation of essential amino acids, by definition, results in numerous, and severe, side effects.

It has been reported that enzymes which degrade non-essential amino acids, such as arginine, may be an effective means of controlling some forms of cancer. For example, arginine deiminase (ADI) isolated from *Pseudomonas pudita* was described by J. B. Jones, "The Effect of Arginine Deiminase on Murine Leukemic Lymphoblasts," Ph.D. Dissertation, The University of Oklahoma, pages 1–165 (1981). Although effective in killing tumor cells in vitro, ADI isolated from *P. pudita* failed to exhibit efficacy in vivo because it had little enzyme activity at a neutral pH and was rapidly cleared from the circulation of experimental animals. Arginine deiminase derived from *Mycoplasma arginini* is described, for example, by Takaku et al, *Int. J. Cancer*, 51:244–249 (1992), and U.S. Pat. No. 5,474,928, the disclosures of which are hereby incorporated by reference herein in their entirety. However, a problem associated with the therapeutic use of such a heterologous protein is its antigenicity. The chemical modification of arginine deiminase from *Mycoplasma arginini*, via a cyanuric chloride linking group, with polyethylene glycol was described by Takaku et al., *Jpn. J. Cancer Res.*, 84:1195–1200 (1993). However, the modified protein was toxic when metabolized due to the release of cyanide from the cyanuric chloride linking group.

There is a need for compositions which degrade non-essential amino acids and which do not have the problems associated with the prior art. The present invention is directed to these, as well as other, important ends.

SUMMARY OF THE INVENTION

The present invention is directed to arginine deiminase modified with polyethylene glycol. In a preferred embodiment, the arginine deiminase is modified with polyethylene glycol, having a total weight average molecular weight of about 1,000 to about 50,000, directly or through a biocompatible linking group.

Another embodiment of the invention is directed to methods of treating cancer, including, for example, sarcomas, hepatomas and melanomas. The invention is also directed to methods of treating and/or inhibiting the metastasis of tumor cells.

These and other aspects of the present invention will be elucidated in the following detailed description of the invention.

BRIEF DESCRIPTION OF THE DRAWINGS

FIG. 1 depicts the amino acid sequences of arginine deiminase cloned from *Mycoplasma arginini* (the top amino acid sequence, SEQ ID NO:1, identified as ADIPROT), *Mycoplasma arthritides* (the middle amino acid sequence, SEQ ID NO:2, identified as ARTADIPRO), and *Mycoplasma hominus* (the bottom amino acid sequence, SEQ ID NO:3, identified as HOMADIPRO).

DETAILED DESCRIPTION OF THE INVENTION

Figure 2A:
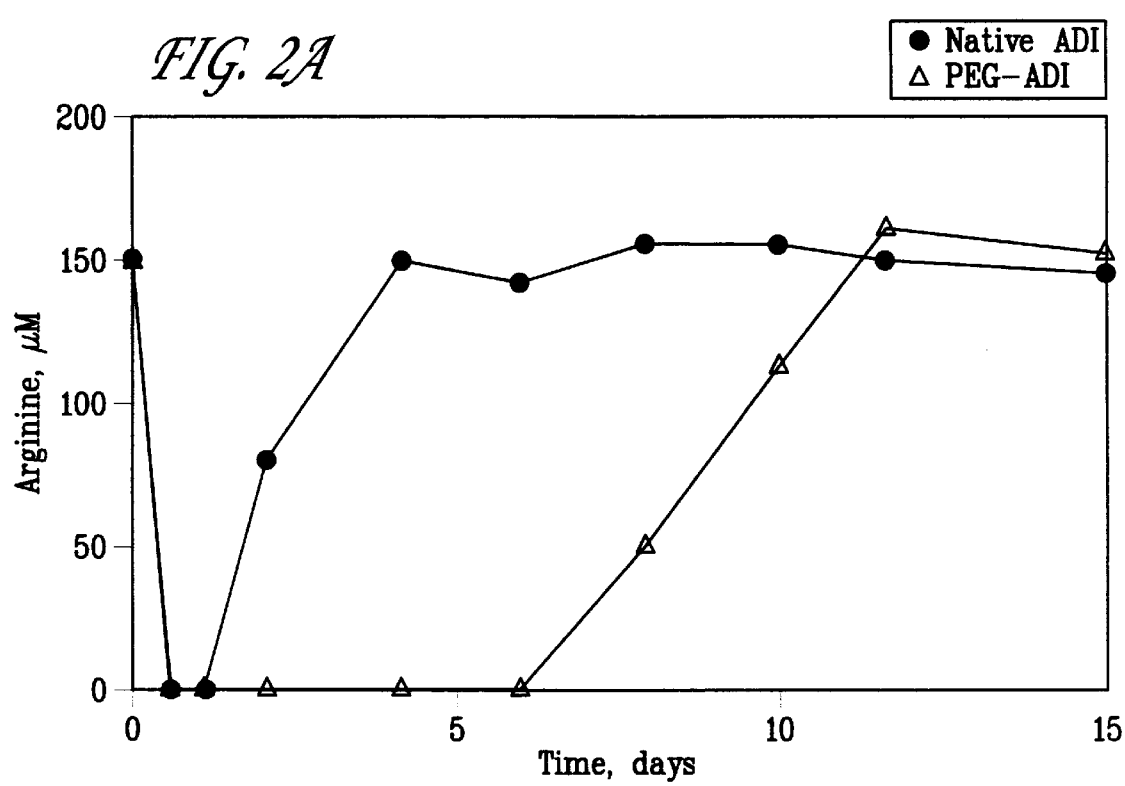
FIGS. 2A and 2B are graphs showing the effect of a single dose of native arginine deiminase and arginine deiminase modified with polyethylene glycol (e.g., molecular weight 5,000) on serum arginine levels and serum citrulline levels in mice.

Normal cells do not require arginine for growth, since they can synthesize arginine from citrulline in a two step process catalyzed by arginosuccinate synthase and arginosuccinate lyase. In contrast, melanomas, hepatomas and some sarcomas do not express arginosuccinate synthase; therefore, they are auxotrophic for arginine. This metabolic difference may be capitalized upon to develop a safe and effective therapy to treat these forms of cancer. Arginine deiminase catalyzes the conversion of arginine to citrulline, and may be used to eliminate arginine. Thus, arginine deiminase may be utilized as a treatment for melanomas, hepatomas and some sarcomas.

Native arginine deiminase may be found in microorganisms and is antigenic and rapidly cleared from circulation in a patient. These problems may be overcome by covalently modifying arginine deiminase with polyethylene glycol (PEG). Arginine deiminase covalently modified with polyethylene glycol (with or without a linking group) may be hereinafter referred to as "ADI-PEG." When compared to native arginine deiminase, ADI-PEG retains most of its enzymatic activity, is far less antigenic, has a greatly extended circulating half-life, and is much more efficacious in the treatment of tumors.

"Polyethylene glycol" or "PEG" refers to mixtures of condensation polymers of ethylene oxide and water, in a branched or straight chain, represented by the general formula $H(OCH_2CH_2)OH$, wherein n is at least 4. "Polyethylene glycol" or "PEG" is used in combination with a numeric suffix to indicate the approximate weight average molecular weight thereof. For example, PEG5,000 refers to polyethylene glycol having a total weight average molecular weight of about 5,000; PEG12,000 refers to polyethylene glycol having a total weight average molecular weight of about 12,000; and PEG20,000 refers to polyethylene glycol having a total weight average molecular weight of about 20,000.

"Melanoma" may be a malignant or benign tumor arising from the melanocytic system of the skin and other organs, including the oral cavity, esophagus, anal canal, vagina, leptomeninges, and/or the conjunctivae or eye. The term "melanoma" includes, for example, acral-lentiginous melanoma, amelanotic melanoma, benign juvenile melanoma, lentigo maligna melanoma, malignant melanoma, nodular melanoma, subungual melanoma and superficial spreading melanoma.

"Hepatoma" may be a malignant or benign tumor of the liver, including, for example, hepatocellular carcinoma.

"Patient" refers to an animal, preferably a mammal, more preferably a human.

"Biocompatible" refers to materials or compounds which are generally not injurious to biological functions and which will not result in any degree of unacceptable toxicity, including allergenic and disease states.

Throughout the present disclosure, the following abbreviations may be used: PEG, polyethylene glycol; ADI, arginine deiminase; SS, succinimidyl succinate; SSA, succinimidyl succinamide; SPA, succinimidyl propionate; and NHS, N-hydroxy-succinimide.

The present invention is based on the unexpected discovery that ADI modified with polyethylene glycol provides excellent results in treating certain types of cancer and inhibiting the metastasis of cancer. ADI may be covalently bonded to polyethylene glycol with or without a linking group, although a preferred embodiment utilizes a linking group.

In the present invention, the arginine deiminase gene may be derived, cloned or produced from any source, including, for example, microorganisms, recombinant biotechnology or any combination thereof. Preferably, arginine deiminase is cloned from microorganisms of the genus Mycoplasma. More preferably, the arginine deiminase is cloned from *Mycoplasma arginini, Mycoplasma hominus, Mycoplasma arthritides,* or any combination thereof. In particular, the arginine deiminase used in the present invention may have one or more of the amino acid sequences depicted in FIG. 1.

In one embodiment of the present invention, the polyethylene glycol (PEG) has a total weight average molecular weight of about 1,000 to about 50,000; more preferably from about 3,000 to about 40,000, more preferably from about 5,000 to about 30,000; more preferably from about 8,000 to about 30,000; more preferably from about 11,000 to about 30,000; even more preferably from about 12,000 to about 28,000; still more preferably from about 16,000 to about 24,000; even more preferably from about 18,000 to about 22,000; even more preferably from about 19,000 to about 21,000, and most preferably about 20,000. Generally, polyethylene glycol with a molecular weight of 30,000 or more is difficult to dissolve, and yields of the formulated product are greatly reduced. The polyethylene glycol may be a branched or straight chain, preferably a straight chain. Generally, increasing the molecular weight of the polyethylene glycol decreases the immunogenicity of the ADI. The polyethylene glycol having a molecular weight described in this embodiment may be used in conjunction with ADI, and, optionally, a biocompatible linking group, to treat cancer, including, for example, melanomas, hepatomas and sarcomas, preferably melanomas.

In another embodiment of the present invention, the polyethylene glycol has a total weight average molecular weight of about 1,000 to about 50,000; preferably about 3,000 to about 30,000; more preferably from about 3,000 to about 20,000; more preferably from about 4,000 to about 12,000; still more preferably from about 4,000 to about 10,000; even more preferably from about 4,000 to about 8,000; still more preferably from about 4,000 to about 6,000; with about 5,000 being most preferred. The polyethylene glycol may be a branched or straight chain, preferably a straight chain. The polyethylene glycol having a molecular weight described in this embodiment may be used in conjunction with ADI, and optionally, a biocompatible linking group, to treat cancer, including, for example, melanomas, hepatomas and sarcomas, preferably hepatomas.

The linking group used to covalently attach ADI to PEG may be any biocompatible linking group. As discussed above, "biocompatible" indicates that the compound or group is non-toxic and may be utilized in vitro or in vivo without causing injury, sickness, disease or death. PEG can be bonded to the linking group, for example, via an ether bond, an ester bond, a thiol bond or an amide bond. Suitable biocompatible linking groups include, for example, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. Preferably, the biocompatible linking group is an ester group and/or a succinimide group. More preferably, the linking group is SS, SPA, SCM, SSA or NHS; with SS, SPA or NHS being more preferred, and with SS or SPA being most preferred.

Alternatively, ADI may be coupled directly to PEG (i.e., without a linking group) through an amino group, a sulfhydral group, a hydroxyl group or a carboxyl group.

ADI may be covalently bonded to PEG, via a biocompatible linking group, using methods known in the art, as described, for example, by Park et al, *Anticancer Res.*, 1:373–376 (1981); and Zaplipsky and Lee, *Polyethylene Glycol Chemistry: Biotechnical and Biomedical Applications*, J. M. Harris, ed., Plenum Press, NY, Chapter 21 (1992), the disclosures of which are hereby incorporated by reference herein in their entirety.

The attachment of PEG to ADI increases the circulating half-life of ADI. Generally, PEG is attached to a primary amine of ADI. Selection of the attachment site of polyethylene glycol on the arginine deiminase is determined by the role of each of the sites within the active domain of the protein, as would be known to the skilled artisan. PEG may be attached to the primary amines of arginine deiminase without substantial loss of enzymatic activity. For example, ADI cloned from *Mycoplasma arginini*, *Mycoplasma arthritides* and *Mycoplasma hominus* has about 17 lysines that may be modified by this procedure. In other words, the 17 lysines are all possible points at which ADI can be attached to PEG via a biocompatible linking group, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. Preferably, ADI is modified with about 7 to about 15 PEG molecules, more preferably from about 9 to about 12 PEG molecules. In other words, about 30% to about 70% of the primary amino groups in arginine deiminase are modified with PEG, preferably about 40% to about 60%, more preferably about 45% to about 55%, and most preferably about 50% of the primary amino groups in arginine deiminase are modified with PEG. When PEG is covalently bonded to the end terminus of ADI, preferably only 1 PEG molecule is utilized. Increasing the number of PEG units on ADI increases the circulating half life of the enzyme. However, increasing the number of PEG units on ADI decreases the specific activity of the enzyme. Thus, a balance needs to be achieved between the two, as would be apparent to one skilled in the art in view of the present disclosure.

In the present invention, a common feature of the most preferred biocompatible linking groups is that they attach to a primary amine of arginine deiminase via a maleimide group. Once coupled with arginine deiminase, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

In the present invention, the particular linking groups do not appear to influence the circulating half-life of PEG-ADI or its specific enzyme activity. However, it is critical to use a biocompatible linking group in the present invention. PEG which is attached to the protein may be either a single chain, as with SS-PEG, SPA-PEG and SC-PEG, or a branched chain of PEG may be used, as with PEG2-NHS. The structural formulas of the preferred linking groups in the present invention are set forth below. SS-PEG:

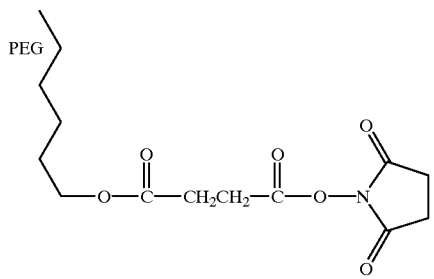

SPA-PEG:

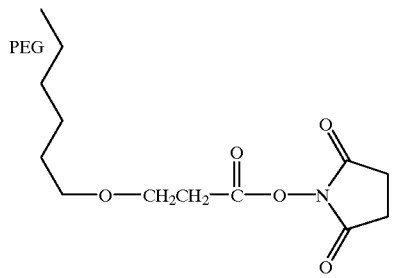

PEG2-NHS:

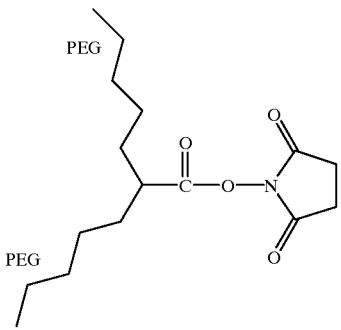

A therapeutically effective amount of one of the compounds of the present invention is an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. The optimum dosage with ADI-SS-PEG5,000 may be about twice a week, while the optimum dosage with ADI-SS-PEG20,000 may be from about once a week to about once every two weeks. PEG-ADI may be mixed with a phosphate buffered saline solution, or any other appropriate solution known to those skilled in the art, prior to injection. The PEG-ADI formulation may be administered as a solid (lyophalate) or as a liquid formulation, as desired.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. As one skilled in the art will recognize, administration of the PEG-ADI composition of the present invention can be carried out, for example, orally, intranasally, intraperitoneally, parenterally, intravenously, intralymphatically, intratumorly, intramuscularly, interstitially, intra-arterially, subcutaneously, intraocularly, intrasynovial, transepithelial, and transdermally.

EXAMPLES

The invention is further demonstrated in the following examples, which are for purposes of illustration, and are not intended to limit the scope of the present invention.

Example 1

Production of Recombinant ADI

Cultures of *Mycoplasma arginini* (ATCC 23243), *Mycoplasma hominus* (ATCC 23114) and *Mycoplasma arthritides* (ATCC 23192) were obtained from the American Type Culture Collection, Rockville, Md.

Arginine deiminase was cloned from *Mycoplasma arginini, Mycoplasma hominus* and *Mycoplasma arthritides* and expressed in *E. coli* as previously described by S. Misawa et al, *J. Biotechnology*, 36:145–155 (1994), the disclosure of which is hereby incorporated herein by reference in its entirety. The amino acid sequences of arginine deiminase from each of the above species is set forth in FIG. 1. The top amino acid sequence, identified as ADIPROT, is from *Mycoplasma arginini;* the middle amino acid sequence, identified as ARTADIPRO, is from *Mycoplasma arthritides;* the bottom amino acid sequence, identified as HOMADIPRO, is from *Mycoplasma hominus*. Each of the amino acid sequences are more than 96% conserved. Characterization, by methods known to those skilled in the art, of each of the proteins with respect to specific enzyme activity, $K_m$, $V_{max}$ and pH optima revealed that they were biochemically indistinguishable from each other. The pH optima was determined using a citrate buffer (pH 5–6.5), a phosphate buffer (pH 6.5–7.5) and a borate buffer (pH 7.5–8.5). The $K_m$ and $V_{max}$ were determined by incubating the enzyme with various concentrations of arginine and quantifying citrulline production. The $K_m$ for the various enzymes was about 0.02 to 0.06 $\mu$M and the $V_{max}$ was about 15–20 $\mu$mol/min/mg, the values of which are within standard error of each other.

The arginine deiminase genes were amplified by polymerase chain reaction using the following primer pair derived from the published sequence of *M. arginini,* as described, for example, by T. Ohno et al, *Infect. Immun.*, 58:3788–3795 (1990), the disclosure of which is hereby incorporated by reference herein in its entirety:

SEQ. ID NO: 4 5'-GCAATCGATGTGTATTTGACAGT-3'

SEQ. ID NO: 5 5'-TGAGGATCCTTACTACCACTTAA-CATCTTTACG-3'

The polymerase chain reaction product was cloned as a Bam H1-Hind III fragment into expression plasmid pQE16. DNA sequence analysis indicated this fragment had the same sequence for the arginine deiminase gene as described by Ohno et al, *Infect. Immun., supra*. The five TGA codons in the ADI gene which encode tryptophan in Mycoplasma were changed to TGG codons by oligonucleotide-directed mutagenesis prior to gene expression in *E. coli,* as taught, for example, by J. R. Sayers et al, *Biotechniques,* 13:592–596 (1992). Recombinant ADI was expressed in inclusion bodies at levels of 10% of total cell protein.

The proteins from each of the above three species of Mycoplasma have approximately 95% homology and are readily purified by column chromatography. Approximately 1.2 g of pure protein may be isolated from 1 liter of fermentation broth. Recombinant ADI is stable for about 2 weeks at 37° C. and for at least 8 months when stored at 4° C. As determined by methods known to those skilled in the art, the proteins had a high affinity for arginine (0.04 $\mu$M), and a physiological pH optima of about 7.2 to about 7.4.

Example 2

Renaturation and Purification of Recombinant ADI

ADI protein was renatured, with minor modifications, as described by Misawa et al, *J. Biotechnology,* 36:145–155 (1994), the disclosure of which is hereby incorporated herein by reference in its entirety. 100 g of cell paste was resuspended in 800 ml of 10 mM $K_2PO_4$ pH 7.0, 1 mM EDTA (buffer 1) and the cells were disrupted by two passes in a Microfluidizer (Microfluidics Corporation, Newton, Mass.). Triton X-100 was added to achieve a final concentration of 4% (v/v). The homogenate was stirred for 30 min at 4° C., then centrifuged for 30 min at 13,000 g. The pellet was collected and resuspended in one liter of buffer 1 containing 0.5% Triton X-100. The solution was diafiltered against 5 volumes of denaturation buffer (50 mM Tris HCl, pH 8.5, 10 mM DTT) using hollow-fiber cartridges with 100 kD retention rating (Microgon Inc., Laguna Hills, Calif.). Guanidine HCl was added to achieve a final concentration of 6 M and the solution was stirred for 15 min at 4° C. The solution was diluted 100-fold into refolding buffer 1, 10 mm $K_2PO_4$, pH 7.0 and stirred for 48 hours at 15° C., particulates were removed by centrifugation at 15,000×g.

The resulting supernatant was concentrated on a Q Sepharose Past Flow (Pharmacia Inc., Piscataway, N.J.) column preequilabrated in refolding buffer. ADI was eluted using refolding buffer containing 0.2 M NaCl. The purification procedure yielded ADI protein, which was >95% pure as estimated by SDS-PAGE analysis. 8 g of pure renatured ADI protein was produced from 1 kg of cell paste which corresponds to 200 mg purified ADI per liter of fermentation.

ADI activity was determined by micro-modification of the method described by Oginsky et al, *Meth. Enzymol.,* (1957) 3:639–642. 10 $\mu$l samples in 0.1 m $Na_2PO_4$, pH 7.0 (BUN assay buffer) were placed in a 96 well microliter plate, 40 $\mu$l of 0.5 mM arginine in BUN assay buffer was added, and the plate was covered and incubated at 37° C. for 15 minutes. 20 $\mu$l of complete BUN reagent (Sigma Diagnostics) was added and the plate was incubated for 10 minutes at 100° C. The plate was then cooled to 22° C. and analyzed at 490 nm by a microliter plate reader (Molecular Devices, Inc). 1.0 IU is the amount of enzyme which converts 1 $\mu$mole of L-arginine to L-citrulline per minute. Protein concentrations were determined using Pierce Coomassie Blue Protein Assay Reagent (Pierce Co., Rockford, Ill.) with bovine serum albumin as a standard.

The enzyme activity of the purified ADI preparations was 17–25 IU/mg.

Example 3

Attachment of PEG to ADI

PEG was covalently bonded to ADI in a 100 mM phosphate buffer, pH 7.4. Briefly, ADI in phosphate buffer was mixed with a 100 molar excess of PEG. The reaction was stirred at room temperature for 1 hour, then the mixture was extensively dialisized to remove unincorporated PEG.

A first experiment was performed where the effect of the linking group used in the PEG-ADI compositions was evaluated. PEG and ADI were covalently bonded via four different linking groups: an ester group or maleimide group, including SS, SSA, SPA and SSPA, where the PEG had a total weight average molecular weight of 5,000, 10,000, 12,000, 20,000, 30,000 and 40,000; an epoxy group, PEG-epoxy, where the PEG had a total weight average molecular weight of 5,000; and a branched PEG group, PEG2-NHS, where the PEG had a total weight average molecular weight of 10,000, 20,000 and 40,000.

Figure 3:
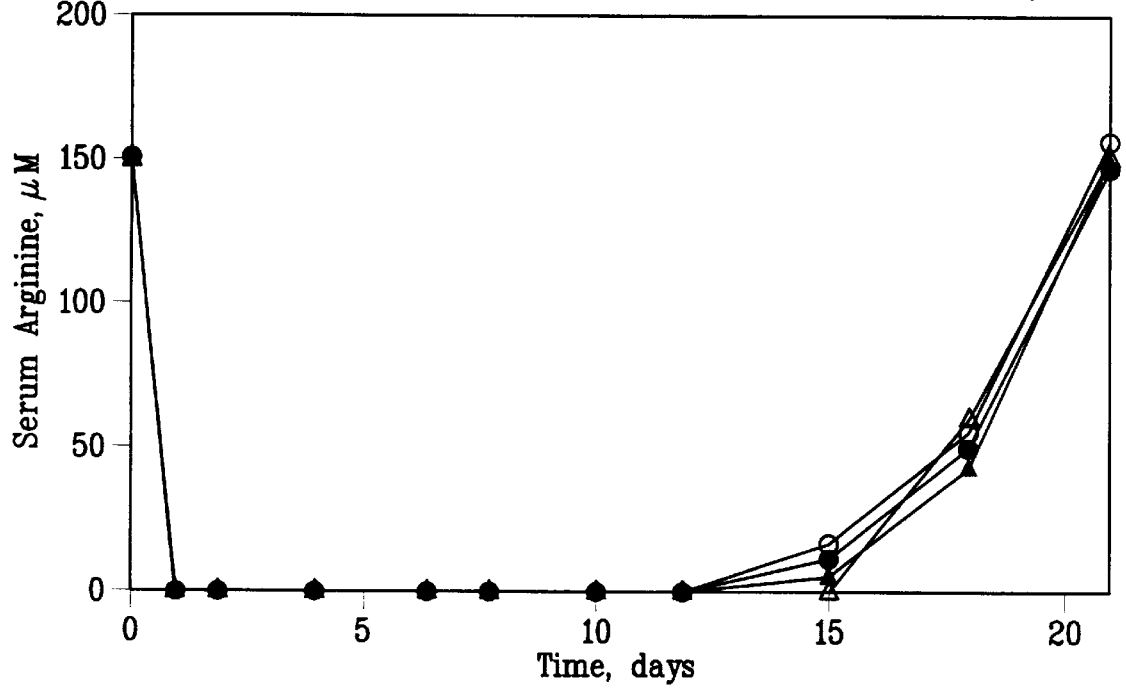
FIG. 3 is a graph showing the effects on serum arginine levels when PEG10,000 is covalently bonded to ADI via various linking groups.

5.0 IU of the resulting compositions were injected into mice (5 mice in each group). To determine the serum levels of arginine, the mice were bled from the retro orbital plexus (100 ul). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for citrulline by this method was approximately 2–6 uM and the reproducibility of measurements within about 8%. The amount of serum arginine was determined by amino acid analysis. As can be seen from the results in FIG. 3, the linking group covalently bonding the PEG and ADI did not have an appreciable effect on the ability of ADI to reduce serum arginine in vivo. In other words, the linking group may not be critical to the results of the experiment, except that a non-toxic linking group must be used for in vivo applications.

A second experiment was performed wherein the effect of the linking group and molecular weight of PEG on serum citrulline levels in vivo was evaluated. Mice (5 in each group) were given various compositions of ADI and PEG-ADI in an amount of 5.0 IU. To determine the serum levels of citrulline, the mice were bled from the retro orbital plexus (100 ul). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for citrulline by this method was approximately 2–6 uM and the reproducibility of measurements within about 8%. The amount of citrulline was determined, and the area under the curve approximated and expressed as $\mu$mol days.

Figure 4:
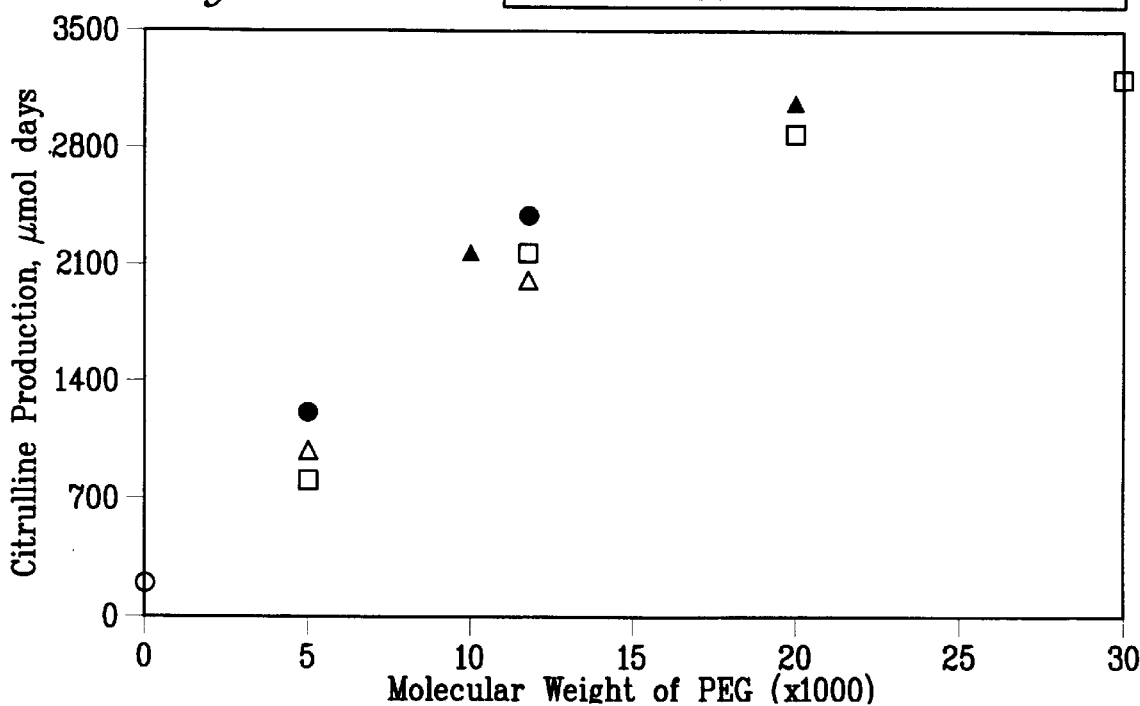
FIG. 4 is a graph showing the effect that the linking group and the molecular weight of the polyethylene glycol have on citrulline production in mice injected with a single dose of PEG-ADI.

In FIG. 4, the open circles indicate the amount of citrulline produced by native ADI, the filled circles are ADI-SC-PEG, the open squares are ADI-SS-PEG, the open triangles are ADI-SPA-PEG, and the filled triangles are branched chain PEG-NHS-PEG$_2$. The results in FIG. 4 demonstrate that the molecular weight of the PEG determines the effectiveness of the PEG-ADI composition. The effectiveness of the PEG-ADI compositions is not necessarily based on the method or means of attachment of the PEG to ADI, except that a biocompatible linking group must be used for in vivo applications.

The results in FIG. 4 also demonstrate that the optimal molecular weight of PEG is 20,000. Although PEG30,000 appears to be superior to PEG20,000 in terms of its pharmacodynamics, PEG30,000 is less soluble, which makes it more difficult to work with. The yields, which were based on the recovery of enzyme activity, were about 90% for PEG5,000 and PEG12,000; about 85% for PEG20,000 and about 40% for PEG30,000. Therefore, PEG20,000 is the best compromise between yield and circulating half life, as determined by citrulline production.

Figure 5A:
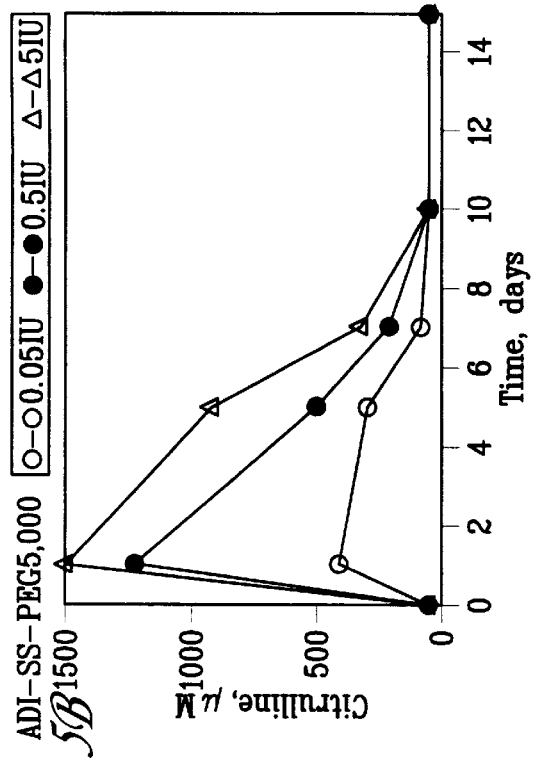
FIGS. 5A and 5B are graphs showing the dose response that ADI-SS-PEG5,000 had on serum arginine and citrulline levels.
Figure 5C:
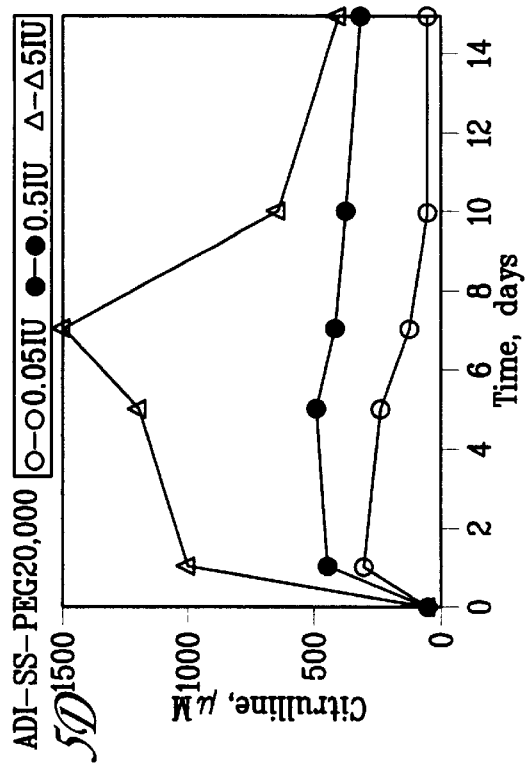
FIGS. 5C and 5D are graphs showing the dose response that ADI-SS-PEG20,000 had on serum arginine and citrulline levels.
Figure 5B:
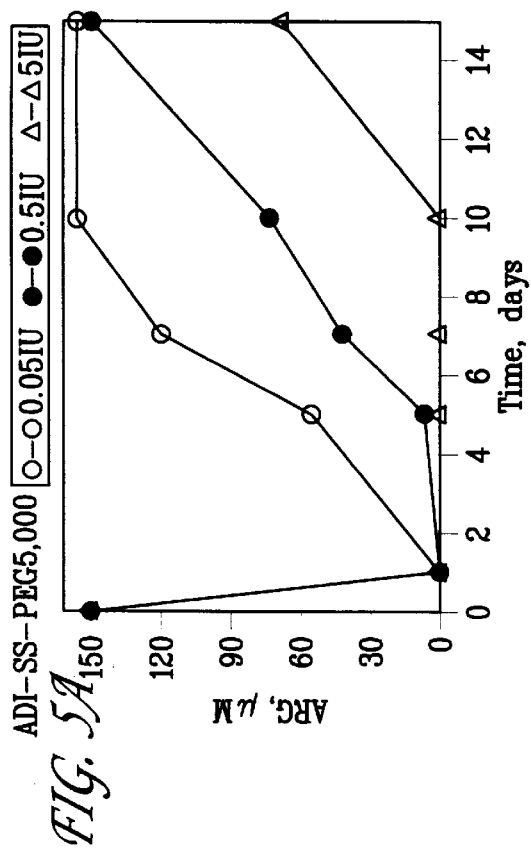
Figure 5D:
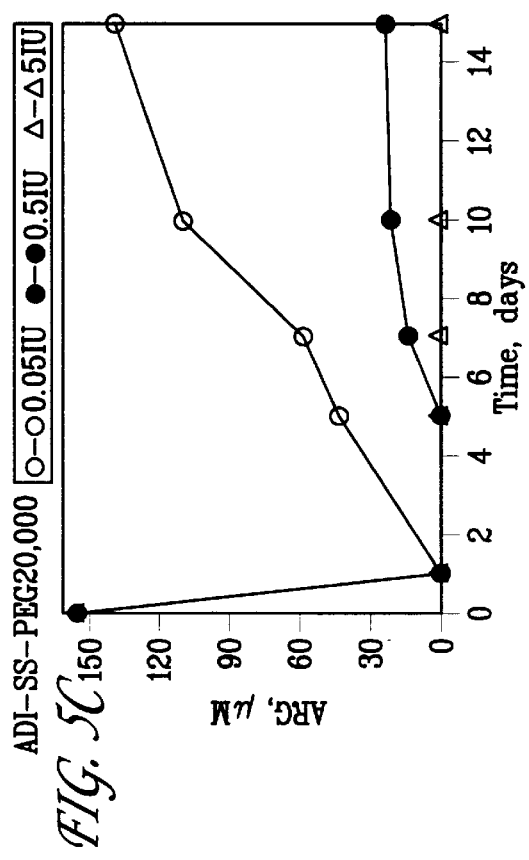

In a third experiment, the dose response of serum arginine depletion and the production of citrulline with ADI-SS-PEG5,000 and ADI-SS-PEG20,000 was determined. Mice (5 in each group) were given a single injection of 0.05 IU, 0.5 IU or 5.0 IU of either ADI-SS-PEG5,000 or ADI-SS-PEG20,000. At indicated times, serum was collected, as described above, and an amino acid analysis was performed to quantify serum arginine (FIGS. 5A and 5C) and serum citrulline (FIGS. 5B and 5D). Both formulations induced a dose dependent decrease in serum arginine and an increase in serum citrulline. However, the effects induced by ADI-SS-PEG20,000 were more pronounced and of longer duration than the effects induced by ADI-SS-PEG5,000.

Example 4

Selectivity of ADI Mediated Cytotoxicity

The selectivity of arginine deiminase mediated cytotoxicity was demonstrated using a number of human tumors. Specifically, human tumors were tested in vitro for sensitivity to ADI-SS-PEG5,000 (50 ng/ml). Viability of cultures was determined after 7 days. For a culture to be defined as "inhibited," greater than 95% of the cells must take up Trypan blue dye. A host of normal cells were also tested, including endothelial cells, smooth muscle cells, epithelial cells and fibroblasts, and none were inhibited by ADI-SS-PEG5,000. Although arginine deiminase has no appreciable toxicity towards normal, and most tumor cells, ADI-SS-PEG5,000 greatly inhibited all human melanomas and hepatomas that were commercially available from the ATCC, MSKCC and Europe.

TABLE 1

Specificity of Arginine Deiminase Cytotoxicity

| Tumor Type | Number of Tumors Tested | Tumors inhibited (%) |
|---|---|---|
| Brain | 16 | 0 |
| Colon | 34 | 0 |
| Bladder | 3 | 0 |
| Breast | 12 | 0 |
| Kidney | 5 | 0 |
| Sarcoma | 11 | 64 |
| Hepatoma | 17 | 100 |
| Melanoma | 37 | 100 |

In a parallel set of experiments, mRNA was isolated from the tumors. Northern blot analyses, using the human arginosuccinate synthase cDNA probe, indicated complete concordance between the sensitivity to arginine deiminase treatment and an inability to express arginosuccinate synthase. This data suggests that ADI toxicity results from an inability to induce arginosuccinate synthase. Therefore, these cells cannot synthesize arginine from citrulline, and are unable to synthesize the proteins necessary for growth.

Example 5

Circulating Half-Life

Balb C mice (5 in each group) were injected intravenously with a single 5.0 IU does of either native arginine deiminase or various formulations of arginine deiminase modified with polyethylene glycol, as indicated in FIGS. 3A and 3B. To determine the serum levels of arginine and citrulline, the mice were bled from the retro orbital plexus (100 ul). Immediately following collection an equal volume of 50% (w/v) of trichloro-acetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for arginine by this method was approximately 6 pM and the reproducibility of measurements within about 8%.

Figure 2B:
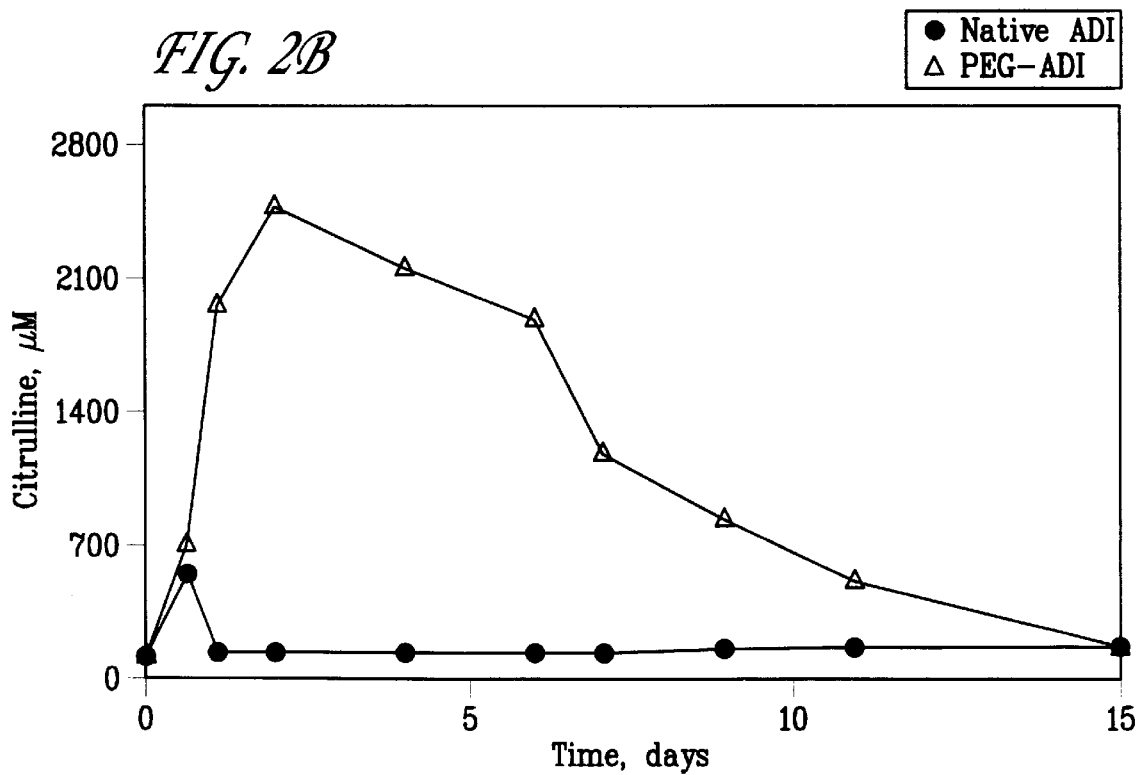

A dose dependent decrease in serum arginine levels, as shown by the solid circles in FIG. 2A, and a rise in serum citrulline, as shown by the open triangles in FIG. 2B, were detected from the single dose administration of native ADI (filled circles) or ADI-SS-PEG (open triangles). However, the decrease in serum arginine and rise in serum citrulline was short lived, and soon returned to normal. The half life of arginine depletion is summarized in the Table below.

TABLE 2

Half-Life of Serum Arginine Depletion

| Compound | Half-Life in Days |
|---|---|
| Native ADI | 1 |
| ADI-SS-PEG5,000 | 5 |
| ADI-SS-PEG12,000 | 15 |
| ADI-SS-PEG20,000 | 20 |
| ADI-SS-PEG30,000 | 22 |

This experiment demonstrates that normal cells and tissues are able to convert the citrulline back into arginine intracellularly while melanomas and hepatomas cannot because they lack arginosuccinate synthetase.

Example 6

Antigenicity of PEG modified ADI

To determine the antigenicity of native ADI, ADI-SS-PEG5,000, and ADI-S-PEG20,000, the procedures described in, for example, Park, *Anticancer Res., supra,* and Kamisaki, *J. Pharmacol. Exp. Ther., supra,* were followed. Briefly, Balb C mice (5 in each group) were intravenously injected weekly for 12 weeks with approximately 0.5 IU (100 ug of protein) of native ADI, ADI-SS-PEG5,000 or ADI-SS-PEG20,000. The animals were bled (0.05 ml) from the retro orbital plexus at the beginning of the experiment and at weeks 4, 8 and 12. The serum was isolated and stored at −70° C. The titers of anti-ADI IgG were determined by ELISA. 50 ug of ADI was added to each well of a 96 well micro-titer plate and was incubated at room temperature for 4 hours. The plates were rinsed with PBS and then coated with bovine serum albumin (1 mg/ml) to block nonspecific protein binding sites, and stored over night at 4° C. The next day serum from the mice was diluted and added to the wells. After 1 hour the plates were rinsed with PBS and rabbit anti-mouse IgG coupled to peroxidase was added to the wells. The plates were incubated for 30 min and then the resulting UV absorbance was measured using a micro-titer plate reader. The titer was defined as the highest dilution of the serum which resulted in a two-fold increase from background absorbance (approximately 0.50 OD).

Figure 6:
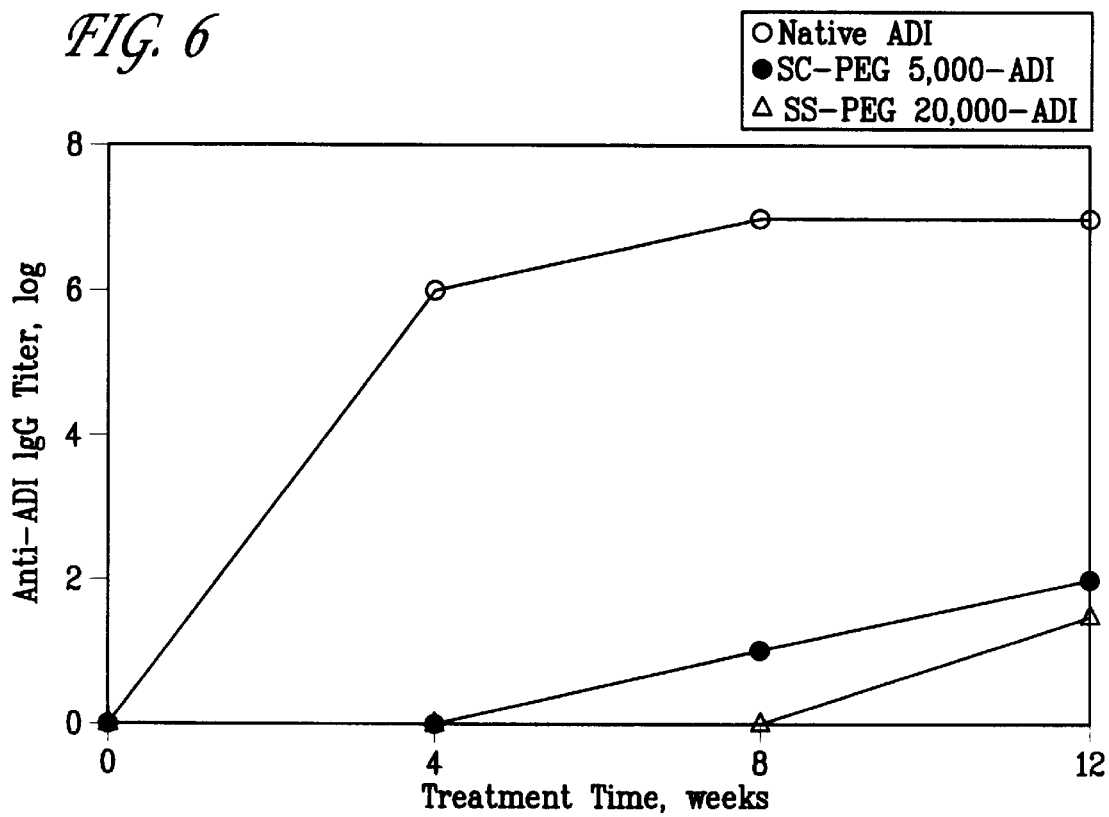
FIG. 6 is a graph showing the antigenicity of native ADI, ADI-SS-PEG5,000, and ADI-SS-PEG20,000.

The results are shown in FIG. 6. The open circles represent the data obtained from animals injected with native ADI, which was very antigenic. The filled circles represent the data obtained from the animals injected with ADI-SS-PEG5,000, while the open triangles represent the data obtained from the animals injected with ADI-SS-PEG20,000. As can be seen from FIG. 6, ADI-SS-PEG5,000 and ADI-SS-PEG20,000 are significantly less antigenic than native ADI. For example, as few as 4 injections of native ADI resulted in a titer of about $10^6$, while 4 injections of any of the PEG-ADI formulations failed to produce any measurable antibody. However, after 8 injections, the ADI-PEG5,000 had a titer of about $10^2$, while ADI-PEG20,000 did not induce this much of an immune response until after 12 injections. The results demonstrate that attaching PEG to ADI blunts the immune response to the protein.

Example 7

Tumor Inhibition of Human Melanomnas

Figure 7:
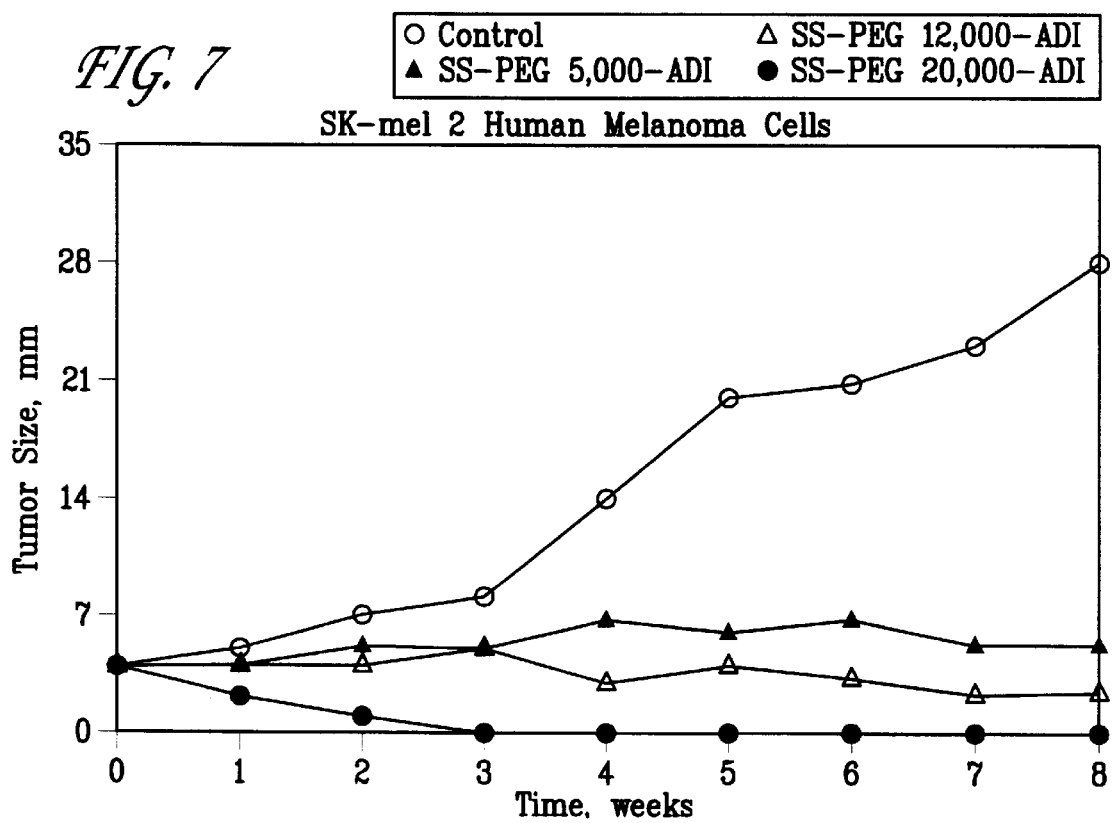
FIG. 7 is a graph showing the effect that treatments with ADI-SS-PEG5,000, ADI-SS-PEG12,000 or ADI-SS-PEG20,000 had on tumor size in mice which were injected with SK-mel 2 human melanoma cells.

The effect of PEG-ADI on the growth of human melanoma (SK-Mel 28) in nude mice was determined. Nude mice (5 in each group) were injected with $10^6$ SK-mel 2 human melanoma cells which were allowed to grow until the tumors reached a diameter of about 3–5 mm. The mice were left untreated (open circles) or were treated once a week for 12 weeks with 5.0 IU of ADI-SS-PEG5,000 (filled triangles), ADI-SS-PEG12,000 (open triangles) or ADI-SS-PEG20,000 (filled circles). The tumor size was measured weekly, and the mean diameter of the tumors is presented in FIG. 7.

Figure 8:
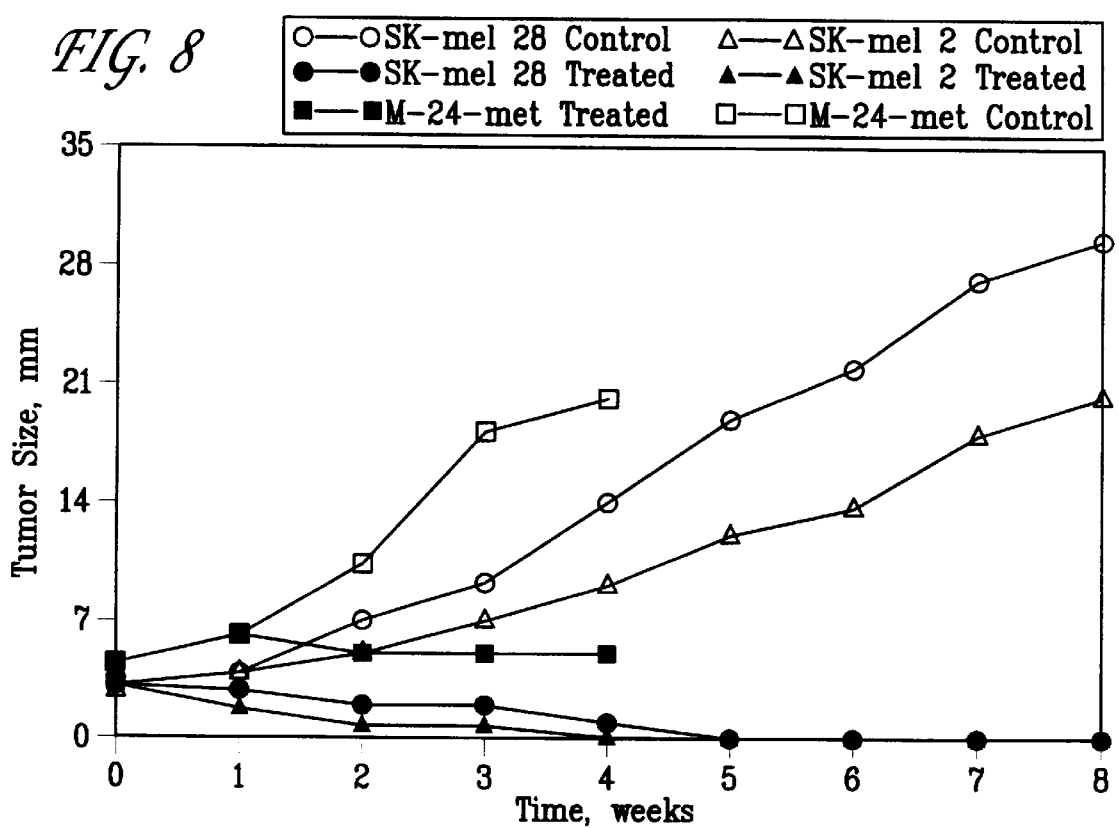
FIG. 8 is a graph showing the effect that treatments with ADI-PEG20,000 had on tumor size in mice which were injected with SK-mel 28, SK-mel 2 or M24-met human melanoma cells.

FIG. 8 shows the effectiveness of ADI-SS-PEG20,000 on three human melanomas (SK-mel 2, SK-mel 28, M24-met) grown in vivo in nude mice. Nude mice (5 in each group) were injected with $10^6$ SK-mel 2, SK-mel 28 or M24-met human melanoma cells. The tumors were allowed to grow until they were approximately 3–5 mm in diameter. Thereafter, the animals were injected once a week with 5.0 IU of ADI-SS-PEG20,000. The results are shown in FIG. 8, and show that PEG-ADI inhibited tumor growth and that eventually the tumors began to regress and disappear. Because the tumors did not have argininosuccinate synthatase, they were unable to synthesize proteins (because ADI eliminated arginine and the tumors could not make it) so that the cells "starved to death."

Since M24-met human melanoma is highly metastatic, the animals injected with M24-met human melanoma cells were sacrificed after 4 weeks of treatment and the number of metastases in the lungs of the animals was determined. The control animals had an average of 32 metastases, while the animals treated with ADI-SS-PEG20,000 did not have any metastases. The results appear to indicate that ADI-SS-PEG20,000 not only inhibited the growth of the primary melanoma tumor, but also inhibited the formation of metastases.

It is of interest to note that in over 200 animals tested, the average number of metastases in the control group was 49±18, while only a single metastasis was observed in 1 treated animal.

Example 8

Tumor Inhibition of Human Hepatomas

Figure 9:
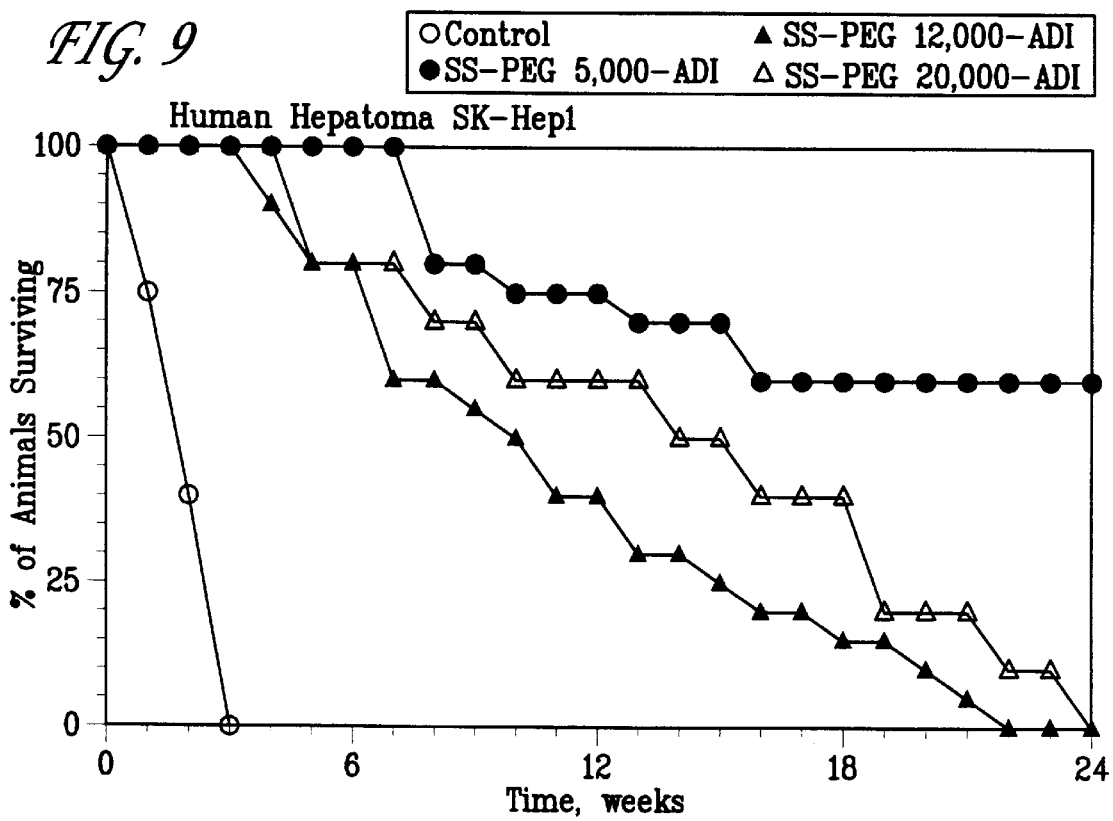
FIG. 9 is a graph showing the effect that treatments with ADI-PEG5,000, ADI-PEG12,000 or ADI-PEG20,000 had on the survival of mice which were injected with human hepatoma SK-Hep1 cells.

The ability of PEG5,000-ADI to inhibit the growth of a human hepatoma in vivo was tested. Nude mice (5 in each group) were injected with $10^6$ human hepatoma SK-Hep1 cells. The tumors were allowed to grow for two weeks and then the animals were treated once a week with 5.0 IU of SS-PEG5,000-ADI (solid circles), SS-PEG12,000-ADI (solid triangles) or SS-PEG20,000-ADI (open triangles). The results are set forth in FIG. 9. The untreated animals (open circles) all died within 3 weeks. In contrast, animals treated with ADI had a far longer life expectancy, as can be seen from FIG. 9. All the surviving mice were euthanized after 6 months, and necropsy indicated that they were free of tumors.

Surprisingly, PEG5,000-ADI is most effective in inhibiting hepatoma growth in vivo. The exact mechanism by which this occurs is unknown. Without being bound to any theory of the invention works, it appears that proteins formulated with SS-PEG5,000-ADI become sequestered in the liver. Larger molecular weights of PEG do not, which may be due to the uniqueness of the hepatic endothelium and the spaces (fenestrae) being of such a size that larger molecular weights of PEG-ADI conjugates are excluded.

Example 9

Application to Humans

PEG5,000-ADI and PEG20,000-ADI were incubated ex vivo with normal human serum and the effects on arginine concentration was determined by amino acid analysis, where the enzyme was found to be fully active and capable of degrading all the detectable arginine with the same kinetics as in the experiments involving mice. The reaction was conducted at a volume of 0.1 ml in a time of 1 hour at 37° C. Additionally, the levels of arginine and citrulline in human serum are identical with that found in mice. PEG-proteins circulate longer in humans than they do in mice. For example, the circulating half life of PEG conjugated adenosine deiminase, asparaginase, glucocerbrocidase, uricase, hemoglobulin and superoxide dismutase all have a circulating half life that is 5 to 10 times longer than the same formulations in mice. What this has meant in the past is that the human dose is most often ⅕ to ⅒ of that used in mice. Accordingly, PEG-ADI should circulate even longer in humans than it does in mice.

Each of the patents, patent applications and publications described herein are hereby incorporated by reference herein in their entirety.

Various modifications of the invention, in addition to those described herein, will be apparent to one skilled in the art in view of the foregoing description. Such modifications are also intended to fall within the scope of the appended claims.

What is claimed is:

1. A compound comprising arginine deiminase covalently bonded via a linking group to polyethylene glycol, wherein the polyethylene glycol has a total weight average molecular weight of from about 1,000 to about 40,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

2. The compound of claim 1, wherein said linking group is a succinimide group.

3. The compound of claim 2, wherein said succinimide group is succinimidyl succinate, succinimidyl propionate, succinimidyl carboxymethylate, succinimidyl succinamide, N-hydroxy succinimide or combinations thereof.

4. The compound of claim 3, wherein said succinimide group is succinimidyl succinate, succinimidyl propionate or combinations thereof.

5. The compound of claim 1, wherein said arginine deiminase is derived from a microorganism of the genus Mycoplasma.

6. The compound of claim 5, wherein said microorganism is selected from the group consisting of *Mycoplasma arginini, Mycoplasma hominus, Mycoplasma arthritides* and combinations thereof.

7. The compound of claim 1, wherein said arginine deiminase is covalently bonded to about 7 to about 15 polyethylene glycol molecules.

8. The compound of claim 7, wherein said arginine deiminase is covalently bonded to about 9 to about 12 polyethylene glycol molecules.

9. The compound of claim 1, wherein said polyethylene glycol has a total weight average molecular weight of from about 10,000 to about 30,000.

10. A method of treating a tumor in a patient comprising administering to said patient the compound of claim 1.

11. The method of claim 10, wherein said tumor is a melanoma.

12. The method of claim 11, wherein said polyethylene glycol has a total weight average molecular weight of about 20,000.

13. The method of claim 11, wherein said linking group is a succinimide group.

14. The method of claim 13, wherein said succinimide group is succinimidyl succinate, succinimidyl propionate, succinimidyl carboxymethylate, succinimidyl succinamide, N-hydroxy succinimide or combinations thereof.

15. The method of claim 10, wherein said tumor is a hepatoma.

16. The method of claim 15, wherein said polyethylene glycol has a total weight average molecular weight of about 5,000.

17. The method of claim 15, wherein said linking group is a succinimide group.

18. The method of claim 17, wherein said succinimide group is succinimidyl succinate, succinimidyl propionate, succinimidyl carboxymethylate, succinimidyl succinamide, N-hydroxy succinimide or combinations thereof.

19. The method of claim 10, wherein said tumor is a sarcoma.

20. A method of treating and inhibiting metastases in a patient comprising administering to said patient the compound of claim 1.

21. A method of enhancing the circulating half life of arginine deiminase comprising modifying said arginine deiminase by covalently bonding said arginine deiminase via a linking group to polyethylene glycol, wherein the polyethylene glycol has a total weight average molecular weight of from about 1,000 to about 40,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

22. A method of enhancing the tumoricidal activity of arginine deiminase comprising modifying said arginine deiminase by covalently bonding said arginine deiminase via a linking group to polyethylene glycol, wherein the polyethylene glycol has a total weight average molecular weight of from about 1,000 to about 40,000, and wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof.

* * * * *